US012285718B2

(12) United States Patent
Al-Ofi

(10) Patent No.: US 12,285,718 B2
(45) Date of Patent: Apr. 29, 2025

(54) AMINE ABSORBER CONFIGURATION

(71) Applicant: SAUDI ARABIAN OIL COMPANY, Dhahran (SA)

(72) Inventor: Saleh H. Al-Ofi, Taplow (GB)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 182 days.

(21) Appl. No.: 17/099,815

(22) Filed: Nov. 17, 2020

(65) Prior Publication Data
US 2022/0152549 A1   May 19, 2022

(51) Int. Cl.
*B01D 53/14* (2006.01)
*B01D 53/18* (2006.01)
(Continued)

(52) U.S. Cl.
CPC ..... *B01D 53/1406* (2013.01); *B01D 53/1425* (2013.01); *B01D 53/1468* (2013.01); *B01D 53/18* (2013.01); *B01D 53/52* (2013.01); *B01D 53/78* (2013.01); *C01B 3/52* (2013.01); *C07C 7/11* (2013.01); *C10L 3/103* (2013.01); *B01D 2252/204* (2013.01); *C01B 2203/0415* (2013.01); *C01B 2203/0485* (2013.01); *C10L 2200/0263* (2013.01); *C10L 2290/545* (2013.01)

(58) Field of Classification Search
CPC ............ B01D 53/1406; B01D 53/1425; B01D 53/1468; B01D 53/18; B01D 53/52; B01D 53/78; B01D 2252/204; C01B 3/52; C01B 2203/0415; C01B 2203/0485; C07C 7/11; C10L 3/103; C10L 220/0263; C10L 2290/545

USPC ....................................... 423/658.3
See application file for complete search history.

(56) References Cited

U.S. PATENT DOCUMENTS 2,299,830 A   10/1942 Legatski et al.
2,523,747 A    9/1950 Weatherby
(Continued)

FOREIGN PATENT DOCUMENTS

CN   102433169 A   5/2012
CN   106479578 A   3/2017
(Continued)

OTHER PUBLICATIONS

"2.2.2.1 Acid gas removal unit", Chapter 2: Gas Conditioning and NGL Recovery Technologies, Handbook of Liquefied Natural Gas, Ed. Saeid Mokhatab et al., 2014, pp. 112-117 (6 pages).
(Continued)

*Primary Examiner* — Anita Nassiri-Motlagh
(74) *Attorney, Agent, or Firm* — Osha Bergman Watanabe & Burton LLP

(57) ABSTRACT

Provided are a process and a system for treating both a high-pressure (HP) and a low-pressure (LP) acid gas-containing gas streams. The system includes a HP absorber unit, a flash drum coupled downstream of the HP absorber unit, and a LP absorber unit coupled downstream of the flash drum. The process includes introducing a HP rich amine solution from a HP absorber unit into a flash drum, operating the flash drum such that a flashed sour gas and a flash drum rich amine solution are produced, and introducing the flashed sour gas and the LP acid gas-containing gas stream into a LP absorber unit.

11 Claims, 1 Drawing Sheet

(51) Int. Cl.
*B01D 53/52* (2006.01)
*B01D 53/78* (2006.01)
*C01B 3/52* (2006.01)
*C07C 7/11* (2006.01)
*C10L 3/10* (2006.01)

(56) References Cited

U.S. PATENT DOCUMENTS

| | | | |
|---|---|---|---|
| 2,662,049 | A | 12/1953 | Magor et al. |
| 2,781,293 | A | 2/1957 | Ragatz |
| 2,998,095 | A | 8/1961 | Mitchell |
| 3,725,252 | A * | 4/1973 | Maier .............. C10G 49/22 |
| | | | 208/213 |
| 5,718,872 | A | 2/1998 | Khanmamedov |
| 5,771,712 | A | 6/1998 | Campbell et al. |
| 2002/0166336 | A1 | 11/2002 | Wilkinson et al. |
| 2004/0060334 | A1 | 4/2004 | Palmer |
| 2010/0183491 | A1 * | 7/2010 | Mazumdar ........ B01D 53/1425 |
| | | | 423/242.1 |
| 2015/0375163 | A1 | 12/2015 | Wen et al. |
| 2018/0222822 | A1 | 8/2018 | van Wagensveld et al. |
| 2019/0001256 | A1 | 1/2019 | Wen |

FOREIGN PATENT DOCUMENTS

| | | |
|---|---|---|
| CN | 107138025 A | 9/2017 |
| WO | 2013022895 A2 | 2/2013 |

OTHER PUBLICATIONS

Gao, Tianyu, et al., "Demonstration of 99% CO2 removal from coal flue gas by amine scrubbing, International Journal of Greenhouse Gas Control", ScienceDirect, Elsevier Ltd., vol. 83, 2019, pp. 236-244 (9 pages).

International Search Report issued in corresponding International Application No. PCT/US2021/059649, mailed Apr. 4, 2022 (5 pages).

Ochieng, Richard, et al., "Amine-based gas-sweetening processes prove economically more viable than the Benfield HiPure process", Jan. 2013, URL: <<https://www.bre.com/PDF/Amine-based-gas-sweetening-processes-prove-economically-more-viable-than-the-Benfield-HiPure-process-OG-2012.PDF>> (26 pages).

Written Opinion issued in corresponding International Application No. PCT/US2021/059649, mailed Apr. 4, 2022 (9 pages).

* cited by examiner

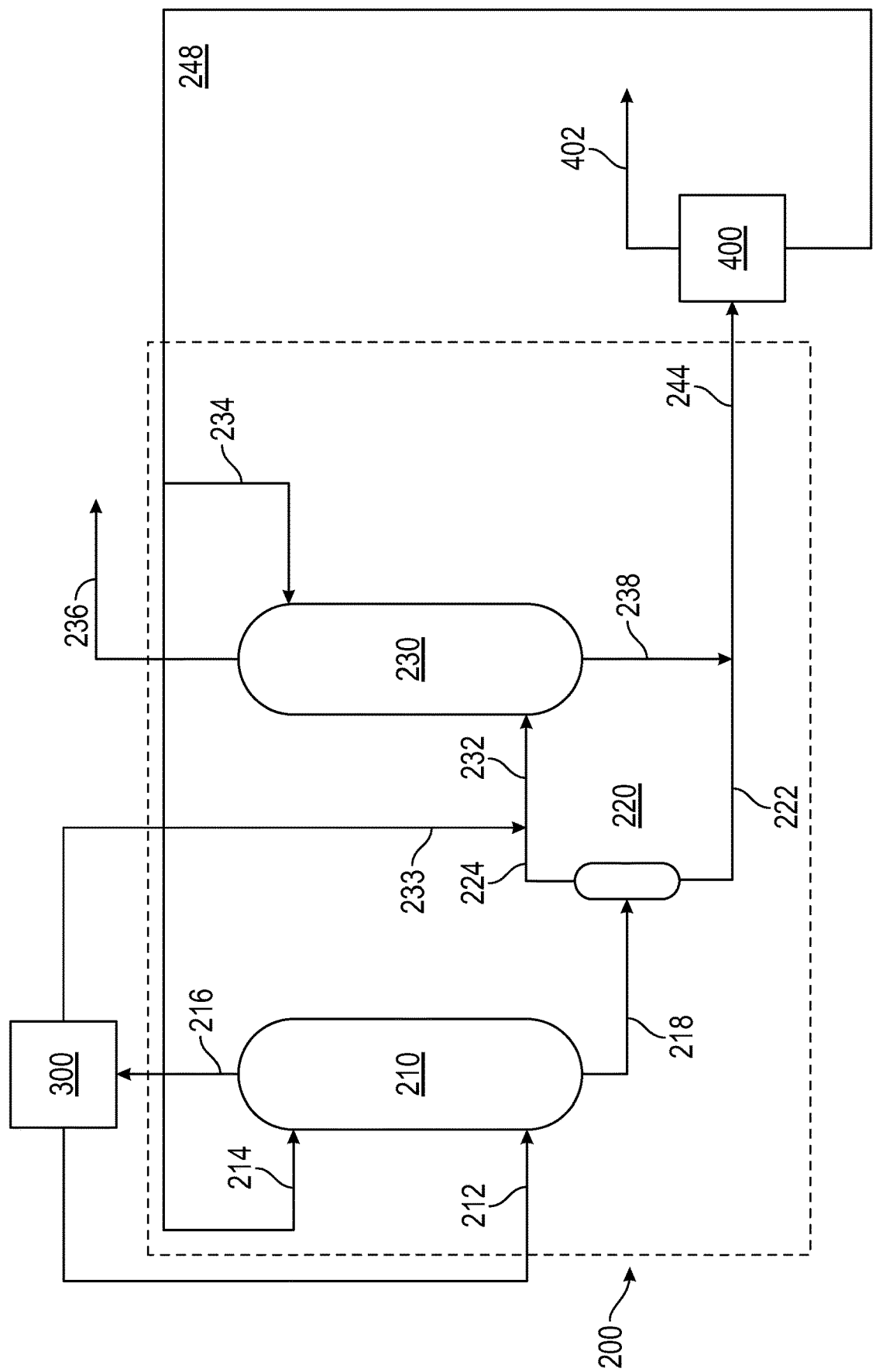

AMINE ABSORBER CONFIGURATION

Amine gas treating is a process that is widely used in refineries, petrochemical plants, natural gas processing plants, and other applications. Amine gas treating, also known as amine scrubbing, gas sweetening, and acid gas removal, is a processes that uses an aqueous amine solution to remove hydrogen sulfide, carbon dioxide, and other "acid gases", from hydrocarbon gas streams. Gas streams containing one or more of the acid gases may be referred to as "sour gas" whether it is from a natural or a fabricated source.

Hydrogen sulfide and carbon dioxide can have separate, individual commercial value. For example, hydrogen sulfide may be converted to elemental sulfur, which can be used in various manufacturing processes. Carbon dioxide can be used in enhanced oil recovery processes, particularly in the miscible flooding of oil reservoirs.

SUMMARY

This summary is provided to introduce a selection of concepts that are further described in the detailed description. This summary is not intended to identify key or essential features of the claimed subject matter, nor is it intended to be used as an aid in limiting the scope of the claimed subject matter.

In an instance of the disclosed subject matter, a process for amine treating an acid gas-containing gas stream is provided. The process includes introducing a rich high-pressure (HP) amine solution from a HP absorber unit into a flash drum. The process also includes operating the flash drum such that a flashed sour gas and a flash drum rich amine solution are produced from the rich HP amine solution. In addition, the process includes introducing the flashed sour gas into a low-pressure (LP) absorber unit.

In another instance of the disclosed subject matter, a system for treating an acid gas-containing stream is provided. The system includes a high-pressure (HP) absorber unit. The HP absorber unit is configured to intimately intermingle a HP hydrogen recycle gas feed and a first lean amine solution to produce a treated HP hydrogen recycle gas and rich HP amine solution. The system also includes a flash drum coupled downstream of the HP absorber unit. The flash drum is configured to flash the rich HP amine solution into a flashed sour gas and a flash drum rich amine solution. The flash drum is configured to operate at a pressure less than the HP absorber unit but greater than the LP absorber unit. The system also includes a low-pressure (LP) absorber unit coupled downstream of the flash drum. The LP absorber unit is configured to intimately intermingle a LP off-gas feed and a second lean amine solution to produce a treated LP off-gas and a rich LP amine solution.

Other aspects and advantages of the claimed subject matter will be apparent from the following description and the appended claims.

BRIEF DESCRIPTION OF DRAWINGS

FIG. 1 is a schematic illustration depicting a system of one or more embodiments of the present disclosure.

In the figures, down is toward or at the bottom and up is toward or at the top of the FIGURE. "Up" and "down" are generally oriented relative to a local vertical direction. However, "upstream" in the oil and gas industry may more generally refer to objects, units or processes taken before a particular unit or process. As well, "downstream" may more generally refer to objects, units or processes taken after a particular unit or process.

DETAILED DESCRIPTION

In refinery process configurations, removal of hydrogen sulfide ($H_2S$) from the recycled high-pressure (HP) hydrogen used in a hydrotreating or hydrocracking process assists in maintaining hydrotreater or hydrocracker catalyst performance In addition, low-pressure (LP) off-gas from these same processes also require $H_2S$ removal such that they can be routed to fuel gas system. Proactively removing hydrogen sulfide from these LP streams avoids corrosion of process piping and fired heater burners. In gas plants, removal of acid gases before contact with a significant amount of water is desirable because the gases and water combine to result in unproductive side reactions, corrode process piping, and other negative outcomes. As such, internal and external specifications and regulations require a significantly reduced amount of acid gases, such as hydrogen sulfide, from hydrocarbon and natural gas streams.

Conventional sour gas removal processes use an aqueous amine solution to remove acid gases. The amine in the solution when at an elevated pressure reacts with hydrogen sulfide to form an acid sulphide in the solution. At these conditions, however, some hydrogen and hydrocarbons may also be absorbed into the amine solution in the high-pressure (HP) absorber. The resultant of the high-pressure absorption process is that a HP sweetened, treated recycle gas (mainly comprised of hydrogen) and a "rich" HP amine solution (containing acid sulphides and unreacted amines) are produced. Similarly, a low-pressure (LP) absorber produces a low-pressure, sweetened, treated off-gas (mainly comprising hydrogen but at reduced purity compared to the HP treated recycle gas) and a rich LP amine solution (again with acid sulphides and unreacted amines). This LP sweetened gas is often used locally as boiler or refinery fuel; however, it may also be compressed and sold. The two rich amine streams from the two absorbers are combined and routed to an amine regeneration unit (ARU), where the amine-hydrogen sulfide reaction is reversed and the $H_2S$ is released back into gaseous form. Hydrogen sulfide is then stripped from the amine solution and passed to the sulphur recovery unit (SRU), where it is used to produce elemental sulphur. The now "lean" amine solution is recycled back to the absorbers. Absorbed hydrocarbons recovered during the stripping of the $H_2S$ are routed to slops. Optionally, a carbon filter may be used to treat the lean amine solution to remove any remaining dissolved hydrocarbons. The resultant lean amine solution would likely have less chance of foaming in an absorber than without the carbon filter treatment.

In some non-embodiment systems, the HP rich amine produced by the HP absorber unit is routed to the LP absorber unit, which may act as a first stage flashing. Such a configuration handles the LP absorber as not only a treatment unit of the low-pressure off-gas but also as a flashing unit for the HP rich amine It is appreciated that such system configurations are for unloading duty from the ARU flash drum. Such a configuration also reduces the HP rich amine stream pressure (and therefore the pipe pressure rating) from the absorbers to the ARU. However, routing the entire rich HP amine solution into the LP absorber unit is not advisable. In doing so, all the dissolved hydrocarbons in the rich amine stream from the HP absorber unit enter the LP absorber unit. Such an operating condition may create a build-up of hydrocarbons in the LP absorber unit that would promote foaming in the column Foaming can shift the H₂S-amine reaction from the bottom of the column (the LP off-gas inlet zone) to the top of the column. Such a situation prevents obtaining the desired H₂S treatment levels as the entire column of the LP absorber unit is not available for absorption and reaction. In severe cases of hydrocarbon build-up and foaming, "amine carry-over" may occur. This is an upset/out-of-control condition that results in amines being carried out of the column and through the low-pressure product gas line of the LP absorber unit.

Along with possibly destabilizing HP absorber unit operations, transferring the entire rich HP amine stream into the LP absorber unit would disrupt the ability of operators and engineers to monitor and troubleshoot the operations of both the HP absorber and the LP absorber unit. In the system configuration previously described, monitoring the H₂S loadings of the rich amine streams from each column is confounded when HP rich amine is introduced into the LP absorber unit—the performance of the LP absorber unit cannot be easily separated from the inputs from the HP absorber unit. It would also be unclear if a process issue developing in the LP absorber unit originated in the LP absorber unit or if it carried over from the HP absorber unit. Compounding such problems from one unit to another is not an appropriate design philosophy for reliable and safe operations. Any upset in the HP absorber unit will automatically transferred to the LP absorber unit, which makes rectifying the upset condition difficult to mitigate. Continuous upset conditions might cause amine solution losses as well as result in lower-quality HP treated hydrogen and LP off-gas streams.

Embodiments in accordance with the present disclosure generally relate to processes and systems for treating "sour gas streams", understood to mean a stream of gas that has a "sour gas" component in it, such as hydrogen sulfide. Generally, embodiments in accordance with the present disclosure involve the utilization of a flash drum positioned in between a high-pressure (HP) absorber unit and a low-pressure (LP) absorber unit. The flash drum is maintained at a pressure slightly greater than the pressure of the LP absorber unit. The pressure drop between the HP absorber unit and the flash drum causes dissolved gases to flash out of the rich HP amine solution. The combination of light hydrocarbons, hydrogen, and hydrogen sulfide (not reacted with the amine) forms a flashed sour gas stream. In turn, the flashed sour gas stream may then be processed in the LP absorber unit. The LP absorber may treat the flashed sour gas stream along with the introduced low-pressure off-gas to produce a sweetened, treated LP off-gas.

For the purposes of the present disclosure, accompanying components that are conventionally used in amine gas treating, such as pumps and compressors, gas handling apparatuses, valves, sensors, electronic controllers, heat exchangers, and mixers, are not shown or discussed for the sake of simplicity, although in an actual operating system these and many more apparatuses and systems would be included. One of ordinary skill in the art appreciates that such components may be included in the embodiments disclosed.

FIG. 1 is a schematic illustration depicting a system of one or more embodiments of the present disclosure. An embodiment amine absorber system 200 includes a high-pressure (HP) absorber unit 210, a flash drum 220, and a low-pressure (LP) absorber unit 230. Flash drum 220 is coupled to the bottom of HP absorber unit 210 such that it receives a rich HP amine solution through rich HP amines line 218. LP absorber unit 230 is coupled to the flash drum 220 where it receives a flashed sour gas.

Outside of embodiment amine absorber system 200, an ARU 400 is shown coupled to the bottom of both the flash drum 220 via flash drum bottoms line 222 and the LP absorber unit 230 via rich LP amines line 238. The ARU 400 in some embodiments receives a combined rich LP amines solution through combined rich amines line 244, completing the "rich" portion of the "amines recycle". In embodiment amine absorber system 200, the HP absorber unit 210 and the LP absorber unit 230 also are both coupled to the ARU 400 through the "lean" portion of the "amines loop". In some instances, the pressure of the lean amine solution passing from the ARU 400 is boosted to a pressure greater than the HP absorber unit. In some embodiments, the ARU 400 provides a combined lean amines solution to amine absorber system 200 via lean amine recycle line 248; however, in other embodiments, first lean amine solution feed line 214 and second lean amine solution feed line 234 may enter amine absorber system 200 separately. In some instances, the pressure of the lean amine solution passing from the ARU 400 is boosted to a pressure greater than the HP absorber unit. As seen in FIG. 1, lean amine recycle line 248 is divided into lean amine solution feed lines 214 and 234. The HP absorber unit 210 receives the first lean amine solution. The LP absorber unit 230 receives the second lean amine solution. This completes an "amines recycle" or "amines loop".

The term "lean" as in a "lean amine solution" refers to the reaction capacity of the amines in the solution, that is, the amines in the amine solution are operable to react with acid gases. A "rich" stream or "rich amine solution", on the other hand, means that a significant portion of the amines in the amine solution have reacted with an acid gas to form acid sulphides and therefore do not have the capacity to perform additional reactions. The reaction is reversible, so when the conditions are reversed, such as in a "regeneration unit", the acid sulphides break down back into the amines in solution and dissolved acid gas. The acid gas bubbles out of the solution and the amine solution is once again "lean".

The ARU of one or more embodiments is not particularly limited and can be any suitable unit for the separation of acid gases from a rich amine known to one of ordinary skill in the art. The ARU may comprise a regenerator unit or column, as previously referenced. The ARU may further comprise an ARU flash drum that is configured to operate at a pressure less than the pressure of the LP absorber unit. The ARU may remove the reacted hydrogen sulfide from the rich amine, generate a lean amine and non-refined hydrogen sulfide gas. The ARU produces the non-refined hydrogen sulfide gas using ARU acid gas line 402. The resulting acid gas stream may be processed by any known process known to one of ordinary skill in the art, such as by reducing hydrogen sulfide to elemental sulfur through a Claus process. The other resultant—a combined lean amines solution—is recycled via lean amine recycle line 248 to start the acid gas extraction process again, as shown in FIG. 1.

HP absorber unit 210 also receives a HP hydrogen recycle gas feed through hydrogen recycle gas feed line 212 and produces a treated HP hydrogen recycle gas through HP treated gas line 216. The HP hydrogen recycle gas feed originates from a hydrotreater or a hydrocracker system, represented as hydrocracker/hydrotreater system 300.

In some embodiments systems, HP hydrogen recycle gas may be derived from a naphtha hydrotreating unit. In some other embodiments, the HP hydrogen recycle gas may be derived from a diesel hydrotreating unit. In yet some other embodiments systems, HP hydrogen recycle gas from a hydrocracker unit. It is understood by one of ordinary skill in the art that for the purposes of this specification that the combined term "hydrocracker/hydrotreater system" is being used to generically refer to several potential systems; it is not a combined system or unit.

The LP absorber unit 230 receives a LP off-gas feed through LP off-gas feed line 232 and produces a treated LP off-gas through LP treated gas line 236. A portion of the LP off-gas feed originates from the hydrocracker/hydrotreater system 300, where a hydrocracking system or a hydrotreating system provides a LP sour off-gas through LP off-gas line 233. The other portion of the LP off-gas feed is the flashed sour gas introduced from flash drum overhead line 224.

In some embodiments systems, LP sour off-gas may be derived from a naphtha hydrotreating unit. In some other embodiments, the LP sour off-gas may be derived from a diesel hydrotreating unit. In yet some other embodiments systems, LP sour off-gas from a hydrocracker unit. In some embodiments systems, the HP hydrogen recycle gas and the LP sour off-gas originate from the same hydrocracking or hydrotreating system.

The HP hydrogen recycle gas feed introduced through hydrogen recycle gas feed line 212 is a light, sour gas. The HP hydrogen recycle gas feed may comprise hydrogen ($H_2$), hydrogen sulfide ($H_2S$), "light" hydrocarbons ($C_{1-4}$), and "medium" hydrocarbons ($C_{5+}$). "Light" hydrocarbons are defined as being hydrocarbons that occur in the gas phase at room temperature and pressure conditions. "Medium" hydrocarbons are defined as being hydrocarbons that occur in the liquid phase at room temperature and pressure conditions.

In some embodiments systems, the HP hydrogen recycle gas feed may be derived from a light or heavy hydrocarbon hydrotreating unit, as previously described. In some other embodiments systems, the HP hydrogen recycle gas feed originates from a hydrocracker unit, as previously described. Regardless of which hydrocracking/hydrotreating system is used, as seen in FIG. 1 the hydrogen recycle gas feed line 212 couples the embodiment amine absorber system to a hydrotreating/hydrocracking system 300 that uses high-pressure hydrogen. The reaction system for hydrotreating and hydrocracking units uses high-pressure hydrogen in the presence of a catalyst to hydrodesulfurize or hydrocrack, respectively, a hydrocarbon feed. This post-reaction hydrogen-containing gas stream (after separation from the hydrocarbon stream of the hydrotreater or hydrocracker) is rich in hydrogen sulfide and some light hydrocarbons. Once the hydrogen is treated in the HP amine absorber, the high-pressure hydrogen is recycled back to the reaction section of the respective hydrotreating or hydrocracking unit.

The HP hydrogen recycle gas feed may have a $H_2$ concentration that is a majority portion of the feed. In one or more embodiments, the HP hydrogen recycle gas feed may be comprised of hydrogen in a concentration having a range of from about 75 mol % (mole percent) to about 90 mol %. In one or more embodiments, the HP hydrogen recycle gas feed may have a hydrogen concentration in a range having a lower limit of any one of 75, 80, and 85 mol %, and an upper limit of any of 80, 85, and 90 mol %, where any lower limit may be used in combination with any mathematically-compatible upper limit. For example, the hydrogen concentration in the HP hydrogen recycle gas feed may be about 82 mol %.

The HP hydrogen recycle gas feed may have a $C_{1-4}$ concentration that is in a range of a significant to substantial portion of the feed. In one or more embodiments, the HP hydrogen recycle gas feed may be comprised of $C_{1-4}$ in a concentration having a range of from about 5 mol % to about 20 mol %. In one or more embodiments, the HP hydrogen recycle gas feed may have a $C_{1-4}$ concentration in a range having a lower limit of any one of 5, 10 and 15 mol %, and an upper limit of any of 10, 15 and 20 mol %, where any lower limit may be used in combination with any mathematically-compatible upper limit. For example, the $C_{1-4}$ concentration in the HP hydrogen recycle gas feed may be about 16 mol %.

The HP hydrogen recycle gas feed may have a $C_{5+}$ concentration that is a detectable portion of the feed. In one or more embodiments, the HP hydrogen recycle gas feed may be comprised of $C_{5+}$ in a concentration having a range of from about 0.0 mol % to about 1 mol %. In one or more embodiments, the HP hydrogen recycle gas feed may have a $C_{5+}$ concentration in a range having a lower limit of any one of 0.0, 0.1, 0.2, 0.3, 0.5, and 0.7 mol %, and an upper limit of any of 0.1, 0.2, 0.3, 0.5, 0.7, and 1.0 mol %, where any lower limit may be used in combination with any mathematically-compatible upper limit. For example, the $C_{5+}$ concentration in the HP hydrogen recycle gas feed may be about 0.8 mol %.

The HP hydrogen recycle gas feed may have a $H_2S$ concentration that is a significant portion of the feed. In one or more embodiments, the HP hydrogen recycle gas feed may be comprised of hydrogen sulfide in a concertation having a range of from about 1.0 mol % to about 3.0 mol %. In one or more embodiments, the HP hydrogen recycle gas feed may have a hydrogen sulfide concentration in a range having a lower limit of any one of 1.0, 1.5, 2.0, and 2.5 mol %, and an upper limit of any of 1.5, 2.0, 2.5, and 3.0 mol %, where any lower limit may be used in combination with any mathematically-compatible upper limit. For example, the hydrogen sulfide concentration in the HP hydrogen recycle gas feed may be about 2.0 mol %.

The pressure and temperature of the HP hydrogen recycle gas feed will generally depend on the system(s) from which it originated, such as from a hydrocracker unit, a naphtha hydrotreating unit, or a diesel hydrotreating unit. In one or more embodiments, the HP hydrogen recycle gas feed may have a pressure in a range of from about 50 to about 150 bars. In one or more embodiments, the HP hydrogen recycle gas feed may have a pressure in a range having a lower limit of any of 50, 60, 70, 80, 90, 100, 110, and 120 bar, and an upper limit of any of 90, 100, 110, 120, 130, 140, and 150 bar, where any lower limit may be used in combination with any mathematically-compatible upper limit. In one or more embodiments, the HP hydrogen recycle gas feed may have a temperature ranging from about 40 to 60° C. In one or more embodiments, the HP hydrogen recycle gas feed may have a temperature in a range having a lower limit of any of 40, 45, 50, and 55° C., and an upper limit of any of 45, 50, 55, and 60° C., where any lower limit may be used in combination with any mathematically-compatible upper limit.

The other feed into the HP absorber unit 210 is a lean amine solution introduced through the lean amine solution feed line 214. The lean amine solution is an aqueous solution comprising one or more amines configured for having reversible reactions with hydrogen sulfide or carbon dioxide, or both. The aqueous fluid of the lean amine solution may include at least one of fresh waters, condensate, and mixtures thereof.

The amine solution is not particularly limited and may comprise an amine that is suitable for the removal of a desired amount of acid gas from the HP hydrogen recycle gas feed. The amines may include one or more amine from the group comprising primary amines, secondary amines, tertiary amines, and combinations thereof. In some embodiments, the amine solution may include, but is not limited to, monoethanolamine (MEA), diethanolamine (DEA), diglycolamine (DGA), diisopropanolamine (DIPA), N-methyldiethanolamine (MDEA), triethanolamine (TEA), piperazine (PZ), 2-amino-2-methyl-1-propanol (AMP), and combinations thereof.

The lean amine solution of one or more embodiments may have an amine concentration in the range of about 15 to 40 percent by weight (wt. %) of the lean amine solution. For example, the lean amine solution of one or more embodiments may have an amine concentration in a range having a lower limit of any of 15, 20, 25, 30, and 35 wt. %, and an upper limit of any of 20, 25, 30, 35, and 40 wt. %, where any lower limit may be used in combination with any mathematically-compatible upper limit. The amine concentration of one or more embodiments may be dependent on the type of the amine used. For example, the lean amine solution may have an amine concentration of about 40 wt. %. In another example, the amine solution may have an amine concentration of about 18 wt. %.

The lean amine solution may have a residual amount of hydrogen sulfide to mitigate equipment and piping corrosion. In some embodiments, the loading of hydrogen sulfide to amine in the lean amine solution is equal to or greater than about 0.010 mol/mol amine, such as in having a hydrogen sulfide loading a range of from about 0.010 to about 0.015 mol/mole amine.

In embodiments of the process, the lean amine solution temperature is maintained at a temperature greater than the temperature of the introduced HP hydrogen recycle gas feed. This is to ensure that the medium hydrocarbons do not condense into the aqueous amine solution in the HP absorber unit readily. Condensation of hydrocarbons in the HP absorber unit may result in foaming within the HP absorber unit. The medium hydrocarbons may act to stabilize otherwise transient bubble formation. This is an undesirable condition for supporting steady-state operations. In some embodiments, the lean amine temperature is maintained at a temperature of about 10° C. greater than the temperature of the HP hydrogen recycle gas feed.

The HP absorber unit of one or more embodiments is configured such that the HP hydrogen recycle gas feed and the lean amine solution intimately intermingle to allow the acid gas absorption into the amine solution. At least a portion of the acid gases, such as hydrogen sulfide, contained in the HP hydrogen recycle gas feed is absorbed by the lean amine solution. This absorbed acid gas may then react with the amine, thereby extracting it from the HP hydrogen recycle gas feed.

In one or more embodiments, the HP absorber unit may be a cylindrical column or tower that is equipped with a gas stream inlet and a gas-distributing device, such as a gas sparger, at the bottom of the column. The HP absorber further includes a lean amine liquid distributor device, such as shower nozzles, at the top of the column. The column also is configured such that there is sufficient mass transfer surface area for the absorption to occur. Common column internal structures, such as distillation trays, structured packing, and random packing, are envisioned. In some embodiments, as HP hydrogen recycle gas feed is generally less dense than the lean amine solution, the introduction of the HP hydrogen recycle gas feed at the bottom of the absorber and the lean amine solution at the top of the absorber results in counter-flow contact as the gas rises and the liquid lean amine solution.

In one or more embodiments, the HP absorber unit may have a temperature ranging from about 40 to 50° C. In further embodiments, the HP absorber may have a temperature in a range having a lower limit of any of 40, 41, 42, 45, 46, 48, and 49° C., and an upper limit of any of 41, 42, 45, 46, 48, 49, and 50° C., where any lower limit may be used in combination with any mathematically-compatible upper limit. In some embodiments, the temperature differential across the HP absorber unit may be about 10 $\Delta°$ C.

In one or more embodiments, the HP absorber unit may have a pressure ranging from about 30 to 150 bar. For example, the pressure of the HP absorber unit may be maintained at about 30 bars if the HP hydrogen recycle gas feed originates from naphtha hydrocarbon hydrotreater process, whereas the pressure may be maintained at about 150 bars if the HP hydrogen recycle gas feed originates from a vacuum gas oil hydrocracking process. In further embodiments, the HP absorber may have a pressure in a range having a lower limit of any of 30, 35, 40, 45, 50, 55, 60, and 75 bars, and an upper limit of any of 40, 50, 70, 90, 110, 130, and 150 bar, where any lower limit may be used in combination with any mathematically-compatible upper limit. In some embodiments, the pressure differential across the HP absorber unit may be about 1 $\Delta$bar.

The resultant products of the exchange are a treated HP hydrogen recycle gas and a rich HP amine solution. As the intimate contact occurs, a portion of acid gas present in the HP hydrogen recycle gas feed is absorbed and then reacted with the amine in the lean amine solution. This removal of acid gases "sweetens" the HP hydrogen gas traversing up in the column. As the amines in solution travel down the column, they convert from lean to rich amines as they react with absorbed sour gases, forming the rich HP amine solution. This also causes more sour gases to dissolve into the amine solution, driving sour gas extraction reaction forward and further purifying the HP hydrogen gas. As well, along the way due to transport phenomenon at the HP absorber unit conditions, a small amount of other gases, such as hydrogen, light hydrocarbons, and medium hydrocarbons, dissolve into the rich HP amine solution. These compounds, unlike the sour gases, do not react with the amines in the rich HP amine solution.

In one or more embodiments, the HP absorber unit 210 may remove about 95 to 99.999 mole % of the hydrogen sulfide introduced with the HP hydrogen recycle gas feed. In further embodiments, the HP absorber may remove an amount of hydrogen sulfide on a mole basis in a range having a lower limit of any of 95, 96, 97, 98, 99, 99.9, and 99.99%, and an upper limit of any of 96, 97, 98, 99, 99.9, 99.99, and 99.999%, where any lower limit may be used in combination with any mathematically-compatible upper limit.

The treated HP hydrogen recycle gas may have a $H_2$ concentration that is a majority portion of the recycle gas. In one or more embodiments, the treated HP hydrogen recycle gas may be comprised of hydrogen in a concentration having a range of from about 75 mol % (mole percent) to about 90 mol %. In one or more embodiments, the treated HP hydrogen recycle gas may have a hydrogen concentration in a range having a lower limit of any one of 75, 80, and 85 mol %, and an upper limit of any of 80, 85, and 90 mol %, where any lower limit may be used in combination with any mathematically-compatible upper limit. For example, the hydrogen concentration in the treated HP hydrogen recycle gas may be about 84 mol %.

The treated HP hydrogen recycle gas may have a $C_{1-4}$ concentration that is in a range of from a significant to substantial portion of the recycle gas. In one or more embodiments, the treated HP hydrogen recycle gas may be comprised of $C_{1-4}$ in a concentration having a range of from about 5 mol % to about 20 mol %. In one or more embodiments, the treated HP hydrogen recycle gas may have a $C_{1-4}$ concentration in a range having a lower limit of any one of 5, 10 and 15 mol %, and an upper limit of any of 10, 15 and 20 mol %, where any lower limit may be used in combination with any mathematically-compatible upper limit. For example, the $C_{1-4}$ concentration in the treated HP hydrogen recycle gas may be about 15 mol %.

The treated HP hydrogen recycle gas may have a $C_{5+}$ concentration that is a detectable portion of the recycle gas. In one or more embodiments, the treated HP hydrogen recycle gas may be comprised of $C_{5+}$ in a concentration having a range of from greater than about 0.0 mol % to about 1 mol %. In one or more embodiments, the treated HP hydrogen recycle gas may have a $C_{5+}$ concentration in a range having a lower limit of any one of greater than 0.0, and 0.1, 0.2, 0.3, 0.5, and 0.7 mol %, and an upper limit of any of 0.1, 0.2, 0.3, 0.5, 0.7, and 1.0 mol %, where any lower limit may be used in combination with any mathematically-compatible upper limit. For example, the $C_{5+}$ concentration in the treated HP hydrogen recycle gas may be about 0.8 mol %.

The treated HP hydrogen recycle gas may have a $H_2S$ concentration that is an incidental portion of the recycle gas. In one or more embodiments, the treated HP hydrogen recycle gas may be comprised of hydrogen sulfide in a concertation having a range of from about 0.001 mol % to about 0.1 mol %. In one or more embodiments, the treated HP hydrogen recycle gas may have a hydrogen sulfide concentration in a range having a lower limit of any one of 0.001, 0.005, 0.01, and 0.05 mol %, and an upper limit of any of 0.005, 0.01, 0.05 and 0.1 mol %, where any lower limit may be used in combination with any mathematically-compatible upper limit. For example, the hydrogen sulfide concentration in the treated HP hydrogen recycle gas may be about 0.001 mol %. In another example, the hydrogen sulfide concentration in the treated HP hydrogen recycle gas may be about 500 ppm (parts per million) (0.05 mol %).

In some embodiments, treated HP hydrogen recycle gas is recycled back to the hydrocracker unit. In some other embodiment, the treated HP hydrogen recycle gas is recycled back to the hydrotreating unit. In either case, the hydrotreating unit or the hydrocracking unit is represented by hydrotreating/hydrocracking system 300 in FIG. 1. The hydrotreating/hydrocracking system 300 is coupled to embodiment amine absorber system 200 via HP treated gas line 216.

The rich HP amine solution from the bottom of the HP absorber unit has several components. Although the composition of the rich HP amine solution mostly contains rich amine (about 35 to about 40 mol %) and water (from about 55 to about 60 mol %), the rich HP amine solution has other components that were merely dissolved in the HP absorber unit that are recoverable and, in some cases, treatable in the LP absorber unit. The rich HP amine solution may have a free $H_2S$ concentration that is significant. For example, in a range of from about 1 to about 4 mol % of the rich HP amine solution may comprise "free" (that is, unreacted with amines; merely dissolved in water) hydrogen sulfide. There are also smaller yet recoverable amounts of hydrogen, light hydrocarbons, and medium hydrocarbons in the rich HP amine solution in rich HP amines line 218.

In one or more embodiments, the rich HP amine solution is passed into flash drum. The flash drum is operated at a reduced pressure compared to the HP absorber unit. This causes the introduced rich amine solution to drop from a greater pressure condition to the reduced pressure condition, creating the "flash" that results in gases escaping the rich amine solution through a turbulent boil. In some configuration of the flash drum, internal structures spread the introduced rich HP amine solution thinly so that the amount of distance a coalescing gas in the liquid has to travel to the surface of the liquid and into the gas phase is reduced, facilitating degassing of the liquid. Atomizing nozzles, packing, distributor plates, and "smash" or "slam" plates (that is, a sacrificial barrier that the fluid is introduced onto to spray the liquid thinly in all directions) are known and appreciated.

The flash drum of one or more embodiments will generally operate at a pressure that is less than the HP absorber unit but at a pressure greater than the LP absorber unit. This facilitates introduction of the rich HP amine solution into the flash drum and the passing of flashed sour gas into the LP absorber unit without the need of a pump (for the rich HP amine solution) or compressor (for the flashed sour gas). In an embodiment, the flash drum is maintained at a pressure greater than the LP absorber unit, such a pressure differential being in a range of from about 1 Δbar to about 3 Δbars, such as about 1 Δbar, about 1.5 Δbars, about 2 Δbars, and about 3 Δbars.

In one or more embodiments, the flash drum may have a pressure ranging from about 9 to about 13 bars, such as about 9, about 10, about 11, about 12 and about 13. In further embodiments, the flash drum may have a pressure in a range having a lower limit of any of 9, 10, 11, and 12, to an upper limit of any of 10, 11, 12, and 13 bars, where any lower limit may be used in combination with any mathematically-compatible upper limit.

In an embodiment, the flash drum is maintained as a temperature less than the HP absorber unit, such a temperature differential being in a range of from about 0.1 Δ° C. to about 3 Δ° C., such as about 1 Δ° C., about 1.5 Δ° C., about 2 Δ° C., and about 3 Δ° C. This differential is due in most part due to the flashing effect that occurs in the flash drum.

The flash drum forms two products from the rich HP amine solution: flashed sour gas and flash drum rich amine solution. The flashed sour gas is passed toward the LP absorber unit 230 through flash drum overhead line 224.

The flashed sour gas may have a $H_2$ concentration that is a majority portion of the gas. In one or more embodiments, the flashed sour gas may be comprised of hydrogen in a concentration of about 50 mol % to about 80 mol %. In one or more embodiments, the flashed sour gas may have a hydrogen concentration in a range having a lower limit of any one of 50, 55, 60, 65, 70, or 75 mol %, and an upper limit of any of 55, 60, 65, 70, 75, or 80 mol %, where any lower limit may be used in combination with any mathematically-compatible upper limit. For example, the hydrogen concentration in the flashed sour gas may be about 75 mol %.

The flashed sour gas may have a $C_{1-4}$ concentration that is a significant portion of the gas. In one or more embodiments, the flashed sour gas may be comprised of $C_{1-4}$ in a concentration having a range of from about 1 mol % to about 10 mol %. In one or more embodiments, the flashed sour gas may be comprised of $C_{1-4}$ concentration in a range having a lower limit of any one of 1, 2, 3, 4, 5, 7, and 9 mol %, and an upper limit of any of 2, 3, 4, 5, 7, 9 and 10 mol %, where any lower limit may be used in combination with any mathematically-compatible upper limit. For example, the $C_{1-4}$ concentration in the flashed sour gas may be about 9 mol %.

The flashed sour gas may have a $C_{5+}$ concentration that is an incidental portion of the gas.

The flashed sour gas may have a $H_2S$ concentration that is a substantial portion of the gas. In one or more embodiments, the flashed sour gas may be comprised of hydrogen sulfide in a concertation having a range of from about 10 mol % to about 20 mol %. In one or more embodiments, the flashed sour gas may have a hydrogen sulfide concentration in a range having a lower limit of any one of 10, 11, 12, 13, 15, 17, 18, or 19 mol %, and an upper limit of any of 11, 12, 13, 15, 17, 18, 19 or 20 mol %, where any lower limit may be used in combination with any mathematically-compatible upper limit. For example, the hydrogen sulfide concentration in the flashed sour gas may be about 17 mol %.

The flash drum rich amine solution from the bottom of the flash drum has several components. Like the rich HP amine solution from which it originated, flash drum rich amine solution mostly contains rich amine (about 35 to about 40 mol %) and water (from about 55 to about 60 mol %). The flash drum rich amine solution passes towards the ARU 400 via flash drum bottoms line 222. In some embodiments, the loading of hydrogen sulfide to amine in the flash drum rich amine solution may be in a range of from about 0.40 to about 0.45 mol/mol amine In some embodiments, the flashed sour gas in flash drum overhead line and the LP sour off-gas are independently and directly introduced into the LP absorber unit. In other embodiments such as shown in FIG. 1, the flashed sour gas in flash drum overhead line 224 is combined with the LP sour off-gas in LP off-gas line 233 to form a LP off-gas feed. The LP off-gas feed is introduced into the LP absorber unit via LP off-gas feed line 232.

The LP sour off-gas may have a $H_2$ concentration that is a majority portion of the off-gas. In one or more embodiments, the LP off-gas may be comprised of hydrogen in a concentration of about 30 mol % to about 70 mol %. In one or more embodiments, the LP off-gas may have a hydrogen concentration in a range having a lower limit of any one of 30, 35, 40, 45, 50, 55, and 60 mol %, and an upper limit of any one of 45, 50, 55, 60, 65, and 70 mol %, where any lower limit may be used in combination with any mathematically-compatible upper limit. For example, the hydrogen concentration in the LP off-gas may be about 50 mol %.

The LP sour off-gas may have a $C_{1-4}$ concentration that is a substantial portion of the off-gas. In one or more embodiments, the LP off-gas may be comprised of $C_{1-4}$ in a concentration of about 10 mol % to about 35 mol %. In one or more embodiments, the LP off-gas may have a $C_{1-4}$ concentration in a range having a lower limit of any one of 10, 15, 20, 25, and 30 mol %, and an upper limit of any one of 15, 20, 25, 30, and 35 mol %, where any lower limit may be used in combination with any mathematically-compatible upper limit. For example, the $C_{1-4}$ concentration in the LP off-gas may be about 32 mol %.

The LP sour off-gas may have a $C_{5+}$ concentration that is a significant portion of the off-gas. In one or more embodiments, the LP off-gas may be comprised of $C_{5+}$ in a concentration of about 0.0 mol % to about 10 mol %. In one or more embodiments, the LP off-gas may have a $C_{5+}$ concentration in a range having a lower limit of any one of 0, 1, 2, 3, 5, and 7 mol %, and an upper limit of any one of 1, 2, 3, 5, 7, and 10 mol %, where any lower limit may be used in combination with any mathematically-compatible upper limit. For example, the $C_{5+}$ concentration in the LP off-gas may be about 6 mol %.

The LP sour off-gas may have a $H_2S$ concentration that is in a range of from a significant to substantial portion of the off-gas. In one or more embodiments, the LP off-gas may be comprised of hydrogen sulfide in a concentration of about 1 mol % to about 15 mol %. In one or more embodiments, the LP off-gas may have a $C_{5+}$ concentration in a range having a lower limit of any one of 1, 2, 3, 5, 7, 8, 10, or 12 mol %, and an upper limit of any one of 2, 3, 5, 7, 8, 10, 12, or 15 mol %, where any lower limit may be used in combination with any mathematically-compatible upper limit. For example, the hydrogen sulfide concentration in the LP off-gas may be about 9 mol %.

The pressure and temperature of the LP sour off-gas will generally be dependent upon its source, such as the operating conditions of the hydrocracker unit, the naphtha hydrotreating unit, or the diesel hydrotreating unit, from which it originated.

The LP sour off-gas has a greater pressure than the LP absorber unit. No compressor is necessary to motivate the LP sour off-gas through either LP off-gas line 233 or LP off-gas feed line 232. In one or more embodiments, the LP sour off-gas may have a pressure ranging from about 9 to about 13 bars. In further embodiments, the LP off-gas may have a pressure in a range having a lower limit of any of 9, 10 ,11, or 12 bars, to an upper limit of any of 10, 11, 12 or 13 bars, where any lower limit may be used in combination with any mathematically-compatible upper limit.

The other feed into the LP absorber unit 230 is the lean amine solution introduced through the lean amine solution feed line 234. The lean amine solution introduced into the LP absorber unit is the same amine solution that is introduced into the HP absorber unit.

In embodiment processes, the amount of first lean amine solution introduced into the HP absorber unit is greater than the amount of second lean amine solution introduced into the LP absorber unit. The difference in the amounts of lean amine solution introduced into the two absorbers is based upon the difference between both the compositions and the relative flow rates of the HP hydrogen recycle gas feed and LP off-gas feed. The volume of gas fed to the HP absorber unit is greater than the amount of gas fed to the LP absorber unit. In addition, the feed into the HP absorber unit is more sour than the feed into the LP absorber unit. The first lean amine solution increases relative to the second lean amine solution as the HP hydrogen recycle gas feed becomes more sour (that is, a greater concentration of introduced sulfur). For example, the amount of first lean amine solution introduced into the HP absorber unit is greater when the HP hydrogen recycle gas feed originates from a vacuum gas oil hydrocracking process versus when it originates from a naphtha hydrocarbon hydrotreater process. The reason for this is that the vacuum gas oil hydrocracking process produces a greater amount of treatable sulfur than the naphtha hydrocarbon hydrotreater process. Both volume and sourness impact the relative amount of lean amine solution between the two absorbers.

The LP absorber unit of the one or more embodiments is configured such that the LP off-gas feed and the lean amine solution intimately intermingle to allow absorption of acid gases. The structure and operation of the LP absorption unit is like that of the HP absorber unit except for the operating conditions, which are at reduced conditions comparatively. At least a portion of the acid gases, such as hydrogen sulfide, contained in the LP off-gas feed is extracted and absorbed by the lean amine solution. The dissolved hydrogen sulfide then reacts with the amine and prevents it from coming out of solution. The resultant products of the exchange are a sweet, treated LP off-gas and a rich LP amine solution.

The LP absorber unit is operated at a reduced temperature compared to the HP absorber unit. In one or more embodiments, the LP absorber unit 230 may have a temperature ranging from about 30 to about 45° C. In further embodiments, the HP absorber unit 210 may have a temperature in a range having a lower limit of any of 30, 33, 36, 39, and 42° C., to and an upper limit of any of 33, 36, 39, 42, and 45° C., where any lower limit may be used in combination with any mathematically-compatible upper limit. In some embodiments, the temperature differential across the LP absorber unit may be about 10 Δ° C.

In embodiments of the process, the lean amine solution temperature is maintained as a temperature greater than the temperature of the introduced LP off-gas feed for similar reasons as previously described with the HP hydrogen recycle gas feed into the HP absorber unit. In some embodiments, the lean amine solution is maintained at a temperature of about 5° C. greater than the temperature of the LP off-gas feed.

The LP absorber unit is operated at a reduced pressure compared to the HP absorber unit and the flash drum. In one or more embodiments, the LP absorber unit 230 may have a pressure ranging from about 7 to about 11 bar. In further embodiments, the LP absorber unit 230 may have a pressure in a range having a lower limit of any of 7, 8, 9, and 10 bar, to an upper limit of any of 8, 9, 10, and 11 bar, where any lower limit may be used in combination with any mathematically-compatible upper limit. In some embodiments, the pressure differential across the HP absorber unit may be about 1 Δbar.

In one or more embodiments, the LP absorber unit 230 may remove about 99.95 to about 99.99 mole % of the hydrogen sulfide introduced with the LP off-gas feed. In further embodiments, the LP absorber unit may remove an amount of hydrogen sulfide on a mole basis in a range having a lower limit of any of 99.95, 99.96, 99.97 and 99.98 mole %, to an upper limit of any of 99.96, 99.97, 99.98, and 99.99 mole %, where any lower limit may be used in combination with any mathematically-compatible upper limit.

The treated LP off-gas may have a $H_2$ concentration that is a majority portion of the off-gas. In one or more embodiments, the treated LP off-gas may be comprised of hydrogen in a concentration of about 30 mol % to about 65 mol %. In one or more embodiments, the treated LP off-gas may have a hydrogen concentration in a range having a lower limit of any one of 30, 35, 40, 45, 50, 55, and 60 mol %, and an upper limit of any of 35, 40, 45, 50, 55, 60, and 65 mol %, where any lower limit may be used in combination with any mathematically-compatible upper limit. For example, the hydrogen concentration in the treated LP off-gas may be about 55 mol %.

The treated LP off-gas may have a $C_{1-4}$ concentration that is a substantial portion of the off-gas. In one or more embodiments, the treated LP off-gas may be comprised of $C_{1-4}$ concentration of from about 10 mol % to about 45 mol %. In one or more embodiments, the treated LP off-gas may have a $C_{1-4}$ concentration in a range having a lower limit of any one of 10, 15, 20, 25, 30, and 35 mol %, and an upper limit of any of 15, 20, 25, 30, 35, 40, and 45 mol %, where any lower limit may be used in combination with any mathematically-compatible upper limit. For example, the $C_{1-4}$ concentration in the treated LP off-gas may be about 33 mol %.

The treated LP off-gas may have a $C_{5+}$ concentration that is a significant portion of the off-gas. In one or more embodiments, the treated LP off-gas may be comprised of $C_{5+}$ concentration of from about 0.5 mol % to about 10 mol %. In one or more embodiments, the treated LP off-gas may have a $C_{5+}$ concentration in a range having a lower limit of any one of 0.5, 1, 2, 3, 5 and 7 mol %, and an upper limit of any of 1, 2, 3, 5, 7, and 10 mol %, where any lower limit may be used in combination with any mathematically-compatible upper limit. For example, the $C_{5+}$ concentration in the treated LP off-gas may be about 6 mol %.

The treated LP off-gas may have a $H_2S$ concentration that is an incidental portion of the off-gas. In one or more embodiments, the treated LP off-gas may be comprised of hydrogen sulfide in a concertation having a range of from about 0.001 mol % to about 0.05 mol %. In one or more embodiments, the treated LP off-gas may have a hydrogen sulfide concentration in a range having a lower limit of any one of 0.001, 0.005, 0.01, and 0.025 mol %, and an upper limit of any of 0.005, 0.01, and 0.025, and 0.05 mol %, where any lower limit may be used in combination with any mathematically-compatible upper limit. For example, the hydrogen sulfide concentration in the treated LP off-gas may be about 0.005 mol % (50 ppm).

In some embodiments, treated LP off-gas is passed to a saturated gas plant for the separation of the mixture of hydrogen, light hydrocarbons, and medium hydrocarbons via the LP treated gas line 236. In other instances, the treated LP off-gas may be used as a refractory or boiler fuel for heat or power generation.

The rich LP amine solution from the bottom of the LP absorber unit 230 has several components. Although the rich LP amine solution mostly contains rich amine (about 40 wt %) and water (about 60 wt %), there may be a residual amount of light and medium hydrocarbon gases as well as "free" hydrogen sulfide in the solution. In some embodiments, the loading of hydrogen sulfide to amine in the LP rich amine solution may be in a range of from about 0.40 to about 0.45 mol/mol amine.

In some embodiments, such as the one shown in FIG. 1, the flash drum rich amine solution and the rich LP amines solution are combined. In such an instance, the combined rich LP amines solution is introduced into the ARU 400 through combined rich amines line 244 to regenerate the lean amine and extract the hydrogen sulfide gas.

In some instances, the pressure of the LP absorber unit may be insufficient to provide adequate drive for the rich LP amine solution to flow towards the ARU. A rich amine solution pump may be used to provide motivation. In such a configuration, the flash drum pressure may be operated such that the pressure of the flash drum rich amine solution is equal to or greater than the pump discharge pressure of the rich LP amine solution. Operating the flash drum in this manner would permit the flash drum rich amine solution to not require a pump to pressurize the solution before its introduction into the ARU.

Although not shown in FIG. 1, in some embodiments of the system a knockout (KO) pot is positioned between the flash drum 220 and the LP absorber unit 230. The KO pot is useful for ensuring that any entrained liquid in either the flashed sour gas or the LP off-gas feed are "knocked out" and collected before the stream enters the LP absorber unit 230. In such embodiments, the KO pot is downstream of where the flashed sour gas and the LP off-gas feed are combined, that is, the KO pot receives a combined feed stream before it enters the LP absorber unit. The knocked-out liquids are passed from the system.

Although the preceding description has been described with reference to particular means, materials and embodiments, it is not intended to be limited to the particulars disclosed; rather, it extends to all functionally equivalent structures, methods and uses, such as are within the scope of the appended claims. In the claims, means-plus-function clauses are intended to cover the structures described as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims except for those in which the claim expressly uses the words 'means for' together with an associated function.

The singular forms "a," "an," and "the" include plural referents, unless the context clearly dictates otherwise.

As used here and in the appended claims, the words "comprise," "has," and "include" and all grammatical variations thereof are each intended to have an open, non-limiting meaning that does not exclude additional elements or steps.

When the words "approximately" or "about" is used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

The term "majority" means greater than 50.00% of the overall composition by the stated unit of measure (mass/volume/mole). The term "substantial" means greater than 10.00% but less than or equal to 50.00% (that is, not a majority) of the overall composition by the stated unit of measure (mass/volume/mole). The term "significant" means greater than 1.00% but less than or equal to 10.00% (that is, not substantial) of the overall composition by the stated unit of measure (mass/volume/mole). The term "detectable" means equal to or greater than 0.01% but less than or equal to 1.00% (that is, not significant) of the overall composition by the stated unit of measure (mass/volume/mole). The term "incidental" means less than 0.01% of the overall composition by the stated unit of measure (mass/volume/mole). However, "incidental" does not exclude the material from the composition; rather, the term indicates that, if determined to be present using industry-available analytical equipment, its presence is de minimus for the purposes of this application.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

Thus, particular implementations of the subject matter have been described. Other implementations are within the scope of the following claims.

What is claimed is:

1. A process for amine treating acid gas-containing gas streams, the process comprising:
    introducing a first lean amine solution and a high pressure hydrogen recycle gas from a hydrocracker or a hydrotreater system directly into a high-pressure (HP) absorber unit, wherein the hydrogen recycle gas has a pressure in a range of from 50 bar to 150 bar and wherein temperature of the first lean amine solution is maintained about 10° C. greater than temperature of a HP hydrogen recycle as feed;
    operating the HP absorber unit such that a rich HP amine solution and a HP treated gas are produced;
    introducing the rich HP amine solution from the HP absorber unit into a flash drum;
    operating the flash drum such that a flashed sour gas and a flash drum rich amine solution are produced from the rich HP amine solution;
    introducing the flashed sour gas into a low-pressure (LP) absorber unit,
    wherein the flash drum is positioned between the HP absorber unit and the LP absorber unit, and wherein the flash drum operates at a pressure in a range of from 1 bar to 3 bar greater than the pressure of the LP absorber unit and at a pressure that is less than a pressure of the HP absorber unit; and
    operating the LP absorber unit such that a rich LP amine solution and a LP treated gas are produced, wherein the LP absorber removes at least 99.95 mole % of the hydrogen sulfide introduced into the LP absorber unit to produce the LP treated gas.

2. The process of claim 1 where the flashed sour gas comprises a majority of hydrogen, a substantial amount of hydrogen sulfide, and a significant amount of light hydrocarbons.

3. The process of claim 1 where the rich HP amine solution comprises a significant amount of "free" hydrogen sulfide.

4. The process of claim 1 further comprising mixing a LP sour off-gas with the flashed sour gas to form a LP off-gas feed; and introducing the LP off-gas feed into the LP absorber unit.

5. The process of claim 4 where the LP sour off-gas comprises a majority of hydrogen, a substantial amount of light hydrocarbons, a substantial amount of medium hydrocarbons, and at least a significant amount of hydrogen sulfide.

6. The process of claim 1 further comprising introducing a second lean amine solution into the LP absorber unit, and operating the LP absorber unit such that a rich LP amine solution and a treated LP off-gas are produced.

7. The process of claim 6 further comprising combining the rich LP amine solution and the flash drum rich amine solution to form a combined LP amine solution; and introducing the combined LP amine solution into an amine recovery unit.

8. The process of claim 7 where the flash drum operates at a pressure such that the pressure of the flash drum rich amine solution is equal to or greater than a pump discharge pressure of the rich LP amine solution such that the flash drum rich amine solution is combined with the LP amine solution downstream of a rich solution pump for the rich LP amine solution.

9. The process of claim 6 where the treated LP off-gas comprises a majority of hydrogen, a substantial amount of light hydrocarbons, a substantial amount of medium hydrocarbons, and an incidental amount of hydrogen sulfide.

10. The process of claim 1 where the HP hydrogen recycle gas feed comprises a majority of hydrogen, at least a significant amount of light hydrocarbons, a detectable amount of medium hydrocarbons, and a significant amount of hydrogen sulfide.

11. The process of claim 1 where the flashed sour gas is introduced into a knock-out (KO) pot before introduction into the LP absorber unit.

\* \* \* \* \*